(12) United States Patent
Ruecroft et al.

(10) Patent No.: US 9,220,708 B2
(45) Date of Patent: Dec. 29, 2015

(54) PHARMACEUTICAL COMPOSITIONS

(75) Inventors: Graham Ruecroft, Wallingford (GB); Dipesh Parikh, Oxford (GB)

(73) Assignee: Prosonix Limited, Oxford, Oxfordshire (GB)

( * ) Notice: Subject to any disclaimer, the term of this patent is extended or adjusted under 35 U.S.C. 154(b) by 0 days.

(21) Appl. No.: 14/237,085

(22) PCT Filed: Aug. 8, 2012

(86) PCT No.: PCT/GB2012/051924
§ 371 (c)(1),
(2), (4) Date: Apr. 4, 2014

(87) PCT Pub. No.: WO2013/021199
PCT Pub. Date: Feb. 14, 2013

(65) Prior Publication Data
US 2014/0228330 A1    Aug. 14, 2014

(30) Foreign Application Priority Data

Aug. 8, 2011 (GB) .................................. 1113662.9

(51) Int. Cl.
| | |
|---|---|
| A61K 31/415 | (2006.01) |
| A61K 31/40 | (2006.01) |
| A61K 9/16 | (2006.01) |
| A61K 31/137 | (2006.01) |
| A61K 31/46 | (2006.01) |
| A61K 31/4704 | (2006.01) |
| A61K 31/522 | (2006.01) |
| A61K 31/58 | (2006.01) |
| A61K 9/00 | (2006.01) |

(52) U.S. Cl.
CPC .............. *A61K 31/40* (2013.01); *A61K 9/0075* (2013.01); *A61K 9/1688* (2013.01); *A61K 31/137* (2013.01); *A61K 31/46* (2013.01); *A61K 31/4704* (2013.01); *A61K 31/522* (2013.01); *A61K 31/58* (2013.01); *A61K 9/008* (2013.01); *A61K 9/0043* (2013.01)

(58) Field of Classification Search
USPC .................. 514/171, 424, 312, 400, 561, 563
See application file for complete search history.

(56) References Cited

U.S. PATENT DOCUMENTS

| | | | |
|---|---|---|---|
| 5,993,836 A | 11/1999 | Castillo | |
| 6,150,418 A * | 11/2000 | Hochrainer et al. | 514/630 |
| 6,433,027 B1 | 8/2002 | Bozung et al. | |
| 6,458,338 B1 * | 10/2002 | Adjei et al. | 424/46 |
| 6,841,161 B1 | 1/2005 | Passmore et al. | |
| 2004/0156928 A1 | 8/2004 | Cordes et al. | |
| 2008/0020008 A1 | 1/2008 | Okazaki et al. | |
| 2009/0285900 A1 * | 11/2009 | Robinson et al. | 424/489 |
| 2010/0189780 A1 | 7/2010 | Walz et al. | |
| 2011/0182830 A1 | 7/2011 | Li et al. | |

FOREIGN PATENT DOCUMENTS

| | | |
|---|---|---|
| CA | 2 368 583 | 11/2000 |
| CN | 1250290 | 4/2006 |
| JP | 2001508793 | 7/2001 |
| JP | 2002538110 | 11/2002 |
| JP | 2002544239 | 12/2002 |
| JP | 2003526629 | 9/2003 |
| JP | 2004510731 | 4/2004 |
| JP | 2005529874 | 10/2005 |
| JP | 2008509196 | 3/2008 |
| WO | 98/51283 | 11/1998 |
| WO | 00/69468 | 11/2000 |
| WO | 0113885 | 3/2001 |
| WO | 2006/013359 | 2/2006 |
| WO | 2007/135409 | 11/2007 |
| WO | 2008/114052 | 9/2008 |
| WO | WO2009153049 | * 12/2009 |
| WO | 2010/007447 | 1/2010 |
| WO | 2010007447 | 1/2010 |
| WO | 2010/085589 | 7/2010 |
| WO | 2010144628 | 12/2010 |

OTHER PUBLICATIONS

Dal Negro et al. CAS: 157: 510340, 2012.*
Shur et al., Pharmaceutical Research, 2009, 26(12): 2657-2666.*
Klous, Bronner, Nuijen, Van Ree and Beijnen, "Pharmaceutical Heroin for Inhalation: Thermal Analysis and Recovery Experiments after Volatilisaton" Journal of Pharmaceutical and Biomedal Analysis, 2005, pp. 944-950.
Japanese Office Action to corresponding JP 2014-524444 patent application, with English translation, dated Jan. 6, 2015, 6 pages.
Chinese Office Action to corresponding CN201280045605.1 patent application, dated Mar. 9, 2015, 6 pages.

* cited by examiner

*Primary Examiner* — Rei-Tsang Shiao

(74) *Attorney, Agent, or Firm* — Tarolli, Sundheim, Covell & Tummino LLP

(57) ABSTRACT

This invention provides a pharmaceutical composition comprising a eutectic composition of two pharmacologically active ingredients for delivery to the lung by inhalation. This invention also provides a pharmaceutical composition comprising a eutectic composition of two pharmacologically active ingredients for the treatment of respiratory disease.

17 Claims, 9 Drawing Sheets

PHARMACEUTICAL COMPOSITIONS

FIELD OF THE INVENTION

The present invention relates to a pharmaceutical composition of two pharmacologically active ingredients for the treatment of chronic respiratory disease.

BACKGROUND OF THE INVENTION

A simple eutectic composition consists of two compounds which are completely miscible in the liquid state but only to a very limited extent in the solid state. The unique property of a eutectic is that it has a lower melting temperature than that of either pure compound. Eutectics have many of the same properties as each phase, but behave differently from either component with respect to melting point, solubility and chemical stability.

A eutectic composition is clearly differentiated from the phenomenon of co-crystal formation. A person skilled in the art will appreciate that in a eutectic composition the two constituent materials are independently crystalline whereas in the case of a co-crystal a completely new crystalline phase forms and in effect replaces the separate crystalline phases with respect to the component molecules within each unit cell. Thus in a co-crystal molecules of both substances are present within the unit cell in an ordered manner.

Solid eutectic compositions may be prepared by rapid cooling of a co-melt of two compounds in order to obtain a physical mixture of very fine crystals of the two components. The preparation of eutectic compositions is a way for formulating drugs which are poorly soluble in gastrointestinal fluids. The active ingredient is mixed with a highly soluble carrier at such proportions that the composition obtained dissolves more easily than the single solid components due to the microcrystalline properties of the combination. This is described in: A. Florence, T. Attwood, Physicochemical Principles of Pharmacy, 4th Ed, Pharmaceutical Press 2006, p. 28.

When the eutectic composition is exposed to the gastrointestinal fluids, the soluble carrier dissolves rapidly, leaving the insoluble drug in an extremely fine state of subdivision. The large surface area of the resulting suspension should result in an enhanced dissolution rate and, consequently, improved bioavailability.

Eutectic compositions are known in the field of local anaesthetics. For example, U.S. Pat. No. 5,993,836 describes a local, topical, transdermal aesthetic formulation comprising a eutectic composition of lidocaine and prilocaine in a defined weight ratio in a lipophilic base. In this eutectic composition, both anaesthetics remain liquid at room temperature and therefore the penetration and absorption of the anaesthetics through the skin is enhanced over applying each anaesthetic separately in crystalline form.

WO 1998/51283 discloses the use of topical pharmaceutical compositions formed by incorporating, in a suitable delivery system, a eutectic composition of at least two pharmacologically active agents, which may be structurally and/or pharmacologically diverse. These compositions achieve enhanced topical permeation for each of the pharmacologically active agents by means of improved drug release from the topical composition itself and not by interaction with the skin. Preferred compositions are those in which the agents possess complementary but different pharmacological activities.

US 2008/0020008 discloses a method of making a eutectic crystalline sugar alcohol designed for improved flavours and taste sensation.

To the best of the inventors' knowledge there is no disclosure of using eutectic compositions in the treatment of respiratory diseases. Further, there is no disclosure of using eutectic compositions in pressurized metered dose inhalers, dry powder inhalers or breath activated nasal inhalers. Further, there is no disclosure of using eutectic compositions which are inhaled into the lung.

Inhalation represents a very attractive, rapid and patient-friendly route for the delivery of systemically acting drugs, as well as for drugs that are designed to act locally on the lungs themselves, such as to treat respiratory diseases, preferably infection or chronic respiratory diseases for example asthma, chronic obstructive pulmonary disease and cystic fibrosis. Not only is it particularly desirable and advantageous to develop technologies for delivering drugs to the lungs in a predictable and reproducible manner but it is important that for concurrent delivery of two or more drugs to the lung the solid-state chemistry of all constituent and mechanically blended mixtures thereof is well understood.

Powder technology, however, for successful dry powders products remains a significant technical hurdle. Formulations must have suitable flow properties, not only to assist in the manufacture and metering of the powders, but also to provide reliable and predictable re-suspension and fluidisation, and to avoid excessive retention of the powder within the dispensing device. The drug particles or particles of pharmacologically active ingredients in the re-suspended powder must aerosolise appropriately so that they can be transported to the appropriate target area within the lung. Typically, for lung deposition, the active particles have a diameter of less than 10 μm, frequently 0.1 to 7 μm or 0.1 to 5 μm.

In this kind of system the interaction between drug-to-drug and drug-to-carrier particles and particle-to-wall are of great importance for successful drug delivery to the deep lung. Turning to drug-to-drug interaction the interaction between particles is determined by adhesion and cohesion forces such as van der Waals, capillary, and coulombic forces. The strength of these forces is affected by the particle size, contact surface area and morphology.

Fine particles 10 μm and smaller, tend to be increasingly thermodynamically unstable as their surface area to volume ratio increases, which provides an increasing surface free energy with this decreasing particle size, and consequently increases the tendency of particles to agglomerate and the strength of the agglomerate. The present invention is concerned with the interaction between particles of different crystalline components.

An additional problem is the variability in surface properties of drug particles. Each pharmacologically active agent powder has its own unique inherent stickiness or surface energy, which can range tremendously from compound to compound. Further, the nature of the surface energies can change for a given compound depending upon how it is processed. For example, high shear blending can lead to significant variations in surface properties because of the aggressive nature of the collisions it employs. Such variations can lead to increased surface energy and increased cohesiveness and adhesiveness. Even in highly regular, crystalline powders, the short range Lifshitz-van der Waals forces can lead to highly cohesive and adhesive powders.

The blended micronized drug particles are loosely agglomerated via Lifshitz-van der Waals forces only. It is important for the function of such a formulation that no capillary forces are formed, because the particle agglomerates must be de-agglomerated in the air stream. Capillary forces are usually several times larger than, for example, Lifshitz-van der Waals forces, and the ability of such an agglomerate to be split into the single particles decreases with increasing autoadhesion forces holding the agglomerates together.

Two common techniques to produce fine particles for dry particle inhalers (DPIs) are mechanical micronization and spray drying. A high-energy milling operation generates particles that are highly charged and thus very cohesive and adhesive if blended with different micronized powders. The produced particles often contain irregular fragments that can form strong aggregates. In addition, multistep processing may cause significant losses of materials during powder production and variability of the product properties from batch to batch. Unlike milling, the spray-drying technique is a one-step continuous process that can directly produce pharmaceutical particles with a desired size. No surfactants or other solubilizing agents are needed in the process. However, the thermal history and drying rate of each particle is difficult to control due to the high flow rates needed in the process and limited controllable parameters. Consequently, the produced particles are usually amorphous and thus sensitive to temperature and humidity variations that may cause structural changes and sintering of the particles during storage of the powder.

It is known to deliver two pharmacologically active ingredients to the lung simultaneously. For example, Advair and Symbicort co-deliver a bronchodilator and a corticosteroid, and therapeutics are known whereby an anticholinergic, such as glycopyrronium bromide, and a bronchodilator, such as indacaterol are administered together. There is a need however, to improve the efficacy of the pharmacologically active ingredients. Further there is a need to improve the delivery of both the pharmacologically active ingredients to the same area in the lung, or the whole of the area of the lung by co-delivery and co-location of the drug within the lung. Further, there is a need to improve the onset time of the pharmacologically active ingredients. Further, there is a need to improve the rate of dissolution of the pharmacologically active ingredient upon deposition as a dry powder within the lung bronchia and alveoli.

SUMMARY OF THE INVENTION

The first aspect of the invention provides a pharmaceutical composition comprising a eutectic composition of two pharmacologically active ingredients for delivery to the lung by inhalation.

The second aspect of the invention provides a pharmaceutical composition comprising a eutectic composition of two pharmacologically active ingredients for the treatment of respiratory disease.

The third aspect of the invention provides a pharmaceutical composition comprising two pharmacologically active ingredients in a eutectic composition, wherein the pharmacologically active ingredients are each independently selected from $\beta_2$ agonists, anticholinergics, corticosteroids, methylxanthine compounds, antihistamines, decongestants, anti-tussive drug substances, PDE I-VI inhibitors, calcium blockers, tobramycin or ciprofloxacin and salts, esters, polymorphs, hydrates or solvates thereof.

The fourth aspect of the invention provides a process for making a composition according to the third aspect of the invention comprising:

providing two pharmacologically active ingredients and:

i) dissolving the two pharmacologically active ingredients in a solvent, removing the solvent; and forming particles of the eutectic composition; or ii) forming a melt of the two active pharmaceutical ingredients, solidifying the melt and forming particles of the eutectic composition; or iii) forming a melt of a first active pharmaceutical ingredient and introducing a solution of a second active pharmaceutical ingredient into the melt, solidifying the resulting composition; and forming particles of the eutectic composition; or iv) subjecting the two pharmacologically active ingredients to mechanical comminution to form particles of the eutectic composition;

wherein the pharmacologically active ingredients are each independently selected from $\beta_2$ agonists, anticholinergics, corticosteroids, methylxanthine compounds, antihistamines, decongestants, anti-tussive drug substances, PDE I-VI inhibitors, calcium blockers, tobramycin or ciprofloxacin and salts, esters, polymorphs, hydrates or solvates thereof.

The pharmaceutical compositions comprising a eutectic composition of two pharmacologically active ingredients of the present invention have advantages in treatment of respiratory diseases. These advantages include improved efficacy of the pharmacologically active ingredients, improvements in the delivery of both the pharmacologically active ingredients to the same area in the lung, or the whole of the area of the lung and improved onset time for the pharmacologically active ingredients. As a consequence of the mutual lowering of the melting points of the respective drug substances there is reduced thermodynamic stability of each drug leading to an increase in both equilibrium solubility and the rate of dissolution of both drugs. A faster rate of dissolution leads to improvement in the onset of action and clinical efficacy. The pharmaceutical compositions of the present invention can be co-located within the lung whereby any synergistic therapeutic action is maximized because of the mutual increase in rate of dissolution and increase in equilibrium solubility of both molecular species when powdered materials are deposited on lung tissue. The effects may be enhanced by increased interaction with lung surfactants such as various phospholipids, primarily dipalmitoyl phosphatidyl choline.

DETAILED DESCRIPTION OF THE INVENTION

The present invention provides a pharmaceutical composition comprising a eutectic composition of two pharmacologically active ingredients for delivery to the lung by inhalation. Eutectic compositions are known in the prior art, but have not been disclosed for delivery to the lung by inhalation.

The present invention also provides pharmaceutical composition comprising a eutectic composition of two pharmacologically active ingredients for the treatment of respiratory disease. Preferably the respiratory disease is chronic respiratory disease, preferably, COPD, asthma or cystic fibrosis. Preferably, the pharmaceutical composition is delivered to the lung by inhalation. Eutectic compositions are known in the prior art, but have not been disclosed for use in treatment of respiratory diseases. Preferably the pharmacologically active ingredients are each independently selected from $\beta_2$ agonists, anticholinergics, corticosteroids, methylxanthine compounds, antihistamines, decongestants, anti-tussive drug substances, PDE I-VI inhibitors, or calcium blockers and salts, esters, polymorphs, hydrates or solvates thereof.

The respiratory disease may be infection. The infection may be in addition to a chronic respiratory disease such as COPD, asthma or cystic fibrosis, or the infection may be unrelated to a chronic respiratory disease. When the respiratory disease to be treated is infection, preferably at least one of the pharmacologically active ingredient is selected from tobramycin and ciprofloxacin and salts, polymorphs, hydrates or solvates thereof and optionally, one of the pharmacologically active ingredient is selected from $\beta_2$ agonists, anticholinergics, corticosteroids, methylxanthine compounds, antihistamines, decongestants, anti-tussive drug substances, PDE I-VI inhibitors, or calcium blockers and salts, esters, polymorphs, hydrates or solvates thereof.

The formation of the eutectic composition depends on the proper concentration of its constituents, which must promote the formation of intermolecular forces attributed to interactions known as hydrogen bridges or van der Waals forces, which counteract the more typical van der Waals forces usual for each component in the formation of individual crystalline forms. The formation of these forces are provided by combining the substances, at molecular level, through i) dissolving the two pharmacologically active ingredients in a solvent, removing the solvent; and forming particles of the eutectic composition; or ii) forming a melt of the two active pharmaceutical ingredients, solidifying the melt and forming particles of the eutectic composition; or iii) forming a melt of a first active pharmaceutical ingredient and introducing a solution of a second active pharmaceutical ingredient into the melt, solidifying the resulting composition; and forming particles of the eutectic composition; or iv) subjecting the two pharmacologically active ingredients to mechanical comminution to form particles of the eutectic composition each method leading to eutectic formation.

Without being bound by theory a binary system consisting of two organic crystalline substances forming a eutectic is amendable to general thermodynamic treatment assuming they are fully miscible in the liquid state and fully immiscible in the crystalline state. Schroeder and van Laar proposed an equation relating the composition of mixtures to their melting points and the termination of fusion $T^f$. It is represented in its simplified format thus:

$$\ln X_A = \Delta H^f_A / R[(T^f_A)^{-1} - (T^f)^{-1}]$$

whereby $X_A$ is the mole fraction of the material A in a mixture with melting terminus at $T^f$; $\Delta H^f_A$ is the enthalpy of fusion of pure component A; $T^f_A$ is the melting terminus of pure component A; and R is the gas constant.

Furthermore, and as described in Thermochimica Acta 404 (2003) 213-226, the thermodynamics of contact melting suggests that it must be entropy-driven. If it is assumed that A and B are two eutectic-forming components the eutectic composition is $X_A$ and $X_B$ (where $X_A = 1 - X_B$) and $T_e$ the eutectic melting temperature. The total entropy change, when compounds A and B melt separately, is given by $$\Delta S_T = X_A \Delta S_A + X_B \Delta S_B$$

where $\Delta S_T$ is the total entropy change, $\Delta S_A$, and $\Delta S_B$ the entropies of fusion of compounds A and B, respectively. The total entropy change however will be $$\Delta S_T = X_A \Delta S_A + X_B \Delta S_B + R X_A \ln(1/X_A) + R X_B \ln(1/X_B) + \Delta S_{ex}$$

where $\Delta S_{ex}$ is the entropy change due to the non-ideal mixing. This relationship shows that $\Delta S_T$ must increase in proportion to the mutual solubility (consistent with Schroeder and van Laar). The lattice energy, or heat of fusion, of the eutectic is a simple weighted sum of the individual components assuming ideal mixing in the liquid state. The melting temperature must decrease due to the increase in entropy (i.e. $T_e = \Delta H_T / \Delta S_T$ where $\Delta H_T$ is the total heat of fusion). The model proposed suggests that intimate contact in the solid state and mutual solubility in the liquid state are the essential criteria for the formation of eutectics.

Intimate contact in the solid state is necessary for contact-induced melting point depression to occur. If eutectic-forming compounds are not in contact, no increase in $\Delta S_T$ would occur, and eutectic melting would not be observed. Eutectic behaviour in tablets or powdered mixtures does not require the eutectic temperature to be exceeded but rather the mixture may form due to mechanical stress, thus facilitating intimate contact between the eutectic-forming materials. The amount of eutectic formed has some proportionality to the amount of intimate contact. For particles of 1 to 5 microns in size with a surface area of 3-10 $m^2$ per gram the intimate contact will be appreciably higher than that for particles of 50 micron and suitable for compaction where the surface area is around 0.5 $m^2$ per gram or 100 microns where the surface area is around 0.25 $m^2$ per gram.

The invention also provides a pharmaceutical composition comprising two pharmacologically active ingredients in a eutectic composition, wherein the pharmacologically active ingredients are each independently selected from $\beta_2$ agonists, anticholinergics, corticosteroids, methylxanthine compounds, antihistamines, decongestants, anti-tussive drug substances, PDE I-VI inhibitors, calcium blockers, tobramycin or ciprofloxacin and salts, esters, polymorphs, hydrates or solvates thereof.

The two pharmacologically active ingredients may be selected from different classes of agents. The two pharmacologically active ingredients may be selected from the same class of agents.

Preferred $\beta_2$ agonists are long acting $\beta_2$ agonists, preferably selected from the group consisting of formoterol, salmeterol, carmoterol, indacaterol, vilanterol, arformoterol, bambuterol, isoproterenol, milveterol, clenbuterol, olodaterol and salts, esters, polymorphs, hydrates or solvates thereof, preferably formoterol fumarate or salmeterol xinafoate. $\beta_2$ agonists may also be short acting $\beta_2$ agonists such as fenoterol, salbutamol, levalbuterol, procaterol, terbutaline, pirbuterol, procaterol, metaproterenol, bitolterol, ritodrine, albuterol and salts, esters, polymorphs, hydrates or solvates thereof, preferably fenoterol hydrobromide.

Preferred anticholinergics are long-acting muscarinic antagonists preferably selected from the group consisting of tiotropium, aclidinium, darotropium, glycopyrrolate, umedlidinium and salts, esters, polymorphs, hydrates or solvates thereof. A preferred short-acting muscarinic antagonist is ipratropium and salts, esters, polymorphs, hydrates or solvates thereof. Particularly preferred muscarinic antagonist are selected from the group consisting of tiotropium bromide, ipratropium bromide, aclidinium bromide, darotropium bromide, glycopyrronium bromide or umeclidinium bromide and salts, esters, polymorphs, hydrates or solvates thereof.

Preferred corticosteroids are selected from the group consisting of mometasone, beclamethasone, budesonide, fluticasone, ciclesonide or triamcinolone and salts, esters, polymorphs, hydrates or solvates thereof, preferably beclamethasone dipropionate, fluticasone propionate, fluticasone furoate, mometasone furoate, or budesonide.

Preferred methylxanthine compounds are selected from the group consisting of theophylline, aminophylline or oxtriphylline and salts, esters, polymorphs, hydrates or solvates thereof.

Preferred antihistamines are selected from the group consisting of acrivastine, cetirizine, desloratadine, fexofenadine, levocetirizine, loratadine, mizolastine, alimemazine, chlorphenamine, clemastine, cyproheptadine, hydroxyzine, ketotifen and promethazine, cimetadine, azatadine, brompheniramine, carbinoxamine or pyrilamine and salts, esters, polymorphs, hydrates or solvates thereof.

Preferred decongestants are selected from the group consisting of pseudoephedrine, oxymetazoline, phenylephrine or xylometazoline and salts, esters, polymorphs, hydrates or solvates thereof.

Preferred anti-tussive drug substances are selected from the group consisting of guaifenesin, carbetapentane, benzonatate, dextromethorphan, hydrocodone, codeine, ephedrine, camphor, menthol, diphenhydramine, phenylpropanolamine, isoaminile, zipeprol, morclofone, prenoxdiazine, dropropizine, piperidione, pentoxyverine, oxolamine, oxeladin, nepinalone, meprotixol, indantadol, dimemorfan, dibunate, cloperastine, clofedanol, butamirate, bibenzonium, benproperine, fedrilate or theobromine and salts, esters, polymorphs, hydrates or solvates thereof.

Preferred phosphodiesterase I-VI inhibitors (PDE I-VI inhibitors) are selected from the group consisting of caffeine, aminophylline, 3-isobutyl-1-methylxanthine, paraxanthine, pentoxifylline, theobromine, theophylline, vinpocetine, erythro-9-(2-hydroxy-3-nonyl)adenine, anagrelide, enoximone, milrinone, mesembrine, rolipram, ibudlast, piclamilast, luteolin, drotaverine, roflumilast, sildenafil, tadalafil, vardenafil, udeafil, avanafil, dipyriidamole; (1-[[5-(1(S)-aminoethly)-2-[8-methoxy-2-(trifluorormethyl)-5-quinolinyl]-4-oxazolyl]carbonyl]-4(R)-[(cyclopropylcarbonyl)amino]-L-proline, ethyl ester xinafoate salt), GSK256066: (6-({3-[(dimethylamino) carbonyl]phenyl}sulfonyl)-8-methyl-4-{[3-methyloxy)phenyl]amino}-3-quinolinecarboxamide) or Roflumimast: (3-cyclopropylmethoxy-4-difluoromethoxy-N-[3,5-dichloropyrid-4-yl]-benzamide and salts, esters, polymorphs, hydrates or solvates thereof.

Preferred phosphodiesterase IV inhibitors (PDE IV inhibitors) are selected from the group consisting of (1-[[5-(1(S)-aminoethly)-2-[8-methoxy-2-(trifluorormethyl)-5-quinolinyl]-4-oxazolyl]carbonyl]-4(R)-[(cyclopropylcarbonyl) amino]-L-proline, ethyl ester xinafoate salt), GSK256066: (6-({3-[(dimethylamino) carbonyl]phenyl}sulfonyl)-8-methyl-4-{[3-methyloxy)phenyl]amino}-3-quinolinecarboxamide) or Roflumimast: (3-cyclopropylmethoxy-4-difluoromethoxy-N-[3,5-dichloropyrid-4-yl]-benzamide and salts, esters, polymorphs, hydrates or solvates thereof.

Preferred calcium blockers are selected from the group consisting of amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine or pranidipine, and salts, polymorphs, hydrates or solvates thereof.

The pharmacologically active ingredients are preferably each independently selected from $\beta_2$ agonists, corticosteroids, methylxanthine compounds, or anticholingerics and salts, polymorphs, hydrates or solvates thereof.

In the present invention, pharmaceutical compositions comprising a eutectic composition are disclosed. A eutectic composition comprises two pharmacologically active ingredients in a specific molar or mass ratio which yields a homogenous crystalline solid-solid dispersion characterized with a single melting point and endotherm of melting. A eutectic composition according to the present invention can comprises more than two pharmacologically active ingredients, such as three or four pharmacologically active ingredients.

In order to determine whether or not a eutectic composition exists or can be found, a person skilled in the art would ordinarily use a number of methods. One such method as employed in this invention involves the intimate physical grinding of mixtures of both constituents in proportions ranging from 0 to 90 mole or mass percent with respect to each component. Each ground sample is subject to determination of melting point and differential scanning calorimetry (DSC) to both verify melting point, the magnitude of the melting point suppression and the magnitude of the endotherm of melting. The formation of a new lower melting component is indicative but not definitive proof of a eutectic composition. With increasing proportions of one substance relative to the other the magnitude of this component as observed on the DSC profile in terms of heat of fusion will increase until a point of homogeneity as indicated by a single melting endotherm event.

Once the eutectic composition has been determined and samples prepared, definitive proof can be established by the technique of X-ray powder diffraction (XRPD). XRPD is a rapid analytical technique primarily used for phase identification of a crystalline material and can provide information on unit cell dimensions. In the present invention the analyzed material is finely ground or prepared by particle engineering techniques as defined in WO 2010/007447 and WO2008/114052, homogenized, and average bulk composition is determined. Crystalline substances act as three-dimensional diffraction gratings for X-ray wavelengths similar to the spacing of planes in a crystal lattice. X-ray diffraction is now a common technique for the study of crystal structures and atomic spacing. X-ray diffraction is based on constructive interference of monochromatic X-rays and a crystalline sample. These X-rays are generated by a cathode ray tube, filtered to produce monochromatic radiation, collimated to concentrate, and directed toward the sample. The interaction of the incident rays with the sample produces constructive interference (and a diffracted ray) when conditions satisfy Bragg's Law ($n\lambda=2d \sin \theta$). This law relates the wavelength of electromagnetic radiation to the diffraction angle and the lattice spacing in a crystalline sample. These diffracted X-rays are then detected, processed and counted. By scanning the sample through a range of $2\theta$ angles, all possible diffraction directions of the lattice should be attained due to the random orientation of the powdered material. Conversion of the diffraction peaks to d-spacings allows identification of the individual substance because each one has a set of unique d-spacings. Typically, this is achieved by comparison of d-spacings with standard reference patterns. A eutectic composition will yield a XRPD pattern consisting of an overlap of the individual pure component XRPD patterns. All diffraction methods are based on generation of X-rays in an X-ray tube. These X-rays are directed at the sample, and the diffracted rays are collected. A key component of all diffraction is the angle between the incident and diffracted rays. Powder and single crystal diffraction vary in instrumentation beyond this.

It is possible to determine by DSC the mass ratio of the pharmacologically active ingredients which form a eutectic composition. From this it is possible to calculate the molar ratio of the pharmacologically active ingredients in the eutectic composition. Eutectic compositions may form based on a unit cell structure and therefore the molar ratio can indicate the unit cell of a eutectic composition. The unit cell structure of a single component crystal relates to the ordered molecular grouping in crystals. The unit cell in turn is replicated many times in a crystal. In a eutectic composition the unit cells of each, or all of the components remain intact as if they were individual components but with intimate mixing at the nanocrystalline or even unit cell dimensions.

The pharmaceutical composition may further comprise an excess of at least one of the pharmacologically active ingredients, wherein the excess forms less than 50 mol % of the amount of the said pharmaceutically active ingredients present in the eutectic composition. That is, if the eutectic composition has a molar ratio of 1:1, in a binary pharmaceutical composition of 50 and 50 mol % there will be a zero (0) mol % excess and the mixture will be 100% eutectic composition; in a binary pharmaceutical composition of 75 and 25 mol % there will be a 50 mol % excess of the major component [50 mol % eutectic composition]; in a binary pharmaceutical composition of 90 and 10 mol % there will be a 80 mol % excess of the major component [20 mol % eutectic composition] and so on. Preferably, the pharmaceutical composition may further comprise an excess of at least one of the pharmacologically active ingredients, wherein the excess forms less than 40 mol %, preferably less than 30 mol % of the amount of the said pharmaceutically active ingredients present in the eutectic composition.

The pharmaceutical composition may have a molar ratio of 10:1 to 1:1, preferably 9:1 to 1:1, preferably 4:1 to 1:1, preferably 2:1 to 1:1. The skilled person can determine the eutectic molar ratio of a given combination of pharmacologically active ingredients by DSC. The skilled person can determine the molar ratio of a specific composition comprising two pharmacologically active ingredients. The skilled person can therefore determine the deviation of a given pharmaceutical composition from the proportion of the eutectic composition as described by molar excess above.

Thus the pharmaceutical composition of the present invention may comprise a mass excess of at least one of the pharmacologically active ingredients. Preferably the excess forms less than 50% by weight, preferably less than 40% by weight, preferably less than 30% by weight of the total weight of the said pharmacologically active ingredients present in the composition. The amount of mass excess of one of the components can be determined by DSC by measuring and integrating the area of the melting endotherm peak corresponding to the excess and measuring and integrating the area of the endotherm peak corresponding to the eutectic composition. Providing the heat of fusion of the excess component in known, the area above and within its respective negative peak as measured in Joules can be converted to a specific molar amount of the excess component.

Preferably at least 90% by weight of at least one of the pharmacologically active ingredients is in the eutectic composition, preferably at least 95% by weight, preferably at least 99% by weight, most preferably substantially all of at least one of the pharmacologically active ingredients is in the eutectic composition. This means that for a given pharmaceutical composition, it is preferable that as much of the pharmacologically active ingredients as possible are in the eutectic composition. Preferably when there are two pharmacologically active ingredients, all of one of them is in the form of a eutectic composition, and optionally there is an excess of the other which is not in the form of a eutectic composition.

Where there is an excess of one of the pharmacologically active ingredients, the composition will show eutectic behaviour, that is the melting point of the composition will be reduced compared to the melting point of either of the pharmacologically active ingredients. There may be different melting points for the composition as a whole, that is, part of the composition may have a lower melting point and other parts a higher melting point. The part of the composition with a lower melting point will be the part in a eutectic. The part of the composition with a higher melting point will be an excess of one of the pharmacologically active ingredients. It may be necessary to have an excess of one of the pharmaceutically active ingredients if the therapeutic ratio of the two pharmacologically active ingredients is different to the eutectic ratio. Such a composition falls within the scope of the present invention because the melting point of at least part of the composition is lower than either of the melting point of either of the two pharmacologically active ingredients.

Theophylline is a methylxanthine compound. It is an inexpensive white crystalline powder used as an oral agent for chronic respiratory diseases such as asthma and COPD.

Theophylline is considered to be a bronchodilator, but it is increasingly recognized that it has other anti-asthma activities, which may be more important and it can be regarded as a useful alternative to other anti-inflammatory drugs for the chronic treatment of mild to moderate asthma. Theophylline is preferably used at lower doses to achieve plasma concentrations of 5-10 mg•/L, which will avoid the risk of side-effects. The role of low-dose theophylline as an adjunct to low-dose inhaled steroids in the management of chronic asthma is very important.

It has been shown that the anti-asthmatic effects of theophylline can supplement those of inhaled steroids in asthma and that the clinical equivalence of theophylline plus steroid to a higher dose of steroid on its own. Theophylline can be used as a steroid-sparing agent.

WO 2006/013359 teaches the use of steroids and methylxanthine compounds such as theophylline, administered at doses which alone are not effective in treating inflammation induced by tobacco smoke (TS) in an animal model of COPD, when administered together have a synergistic effect and are able to markedly reduce inflammation in said models, by 50% or more in the tests. TS exposure is widely accepted to be the principal cause of COPD in human beings. In effect theophylline is administered at a dose which, in isolation, is not effective in treating said respiratory disease, but together with the steroid is effective in reducing inflammation in the respiratory tract. Preferably, the chronic disease is COPD. Advantageously, the chronic disease may include severe asthma and cystic fibrosis.

The pharmaceutical composition may comprise two pharmacologically active ingredients in a eutectic composition, wherein the pharmacologically active ingredients are a corticosteroid and a methylxanthine compound. Preferably the methylxanthine compound is theophylline, aminophylline or oxtriphylline and salts, esters, polymorphs, hydrates or solvates thereof, preferably theophylline.

The corticosteroid and methylxanthine compound are preferably in a specific molar ratio, typically 1:1 molar ratio in a solid-state eutectic composition. A specific combination of the methylxanthine compound, preferably theophylline and corticosteroid, such as the preferred corticosteroids has maximum interaction between the two crystalline species yielding homogeneity of melt and definition of a single eutectic melting point. The eutectic composition can be the pharmacological relevant molar ratio of 1:1. Theophylline has been shown to restore steroid responsiveness in patients with COPD and enhances the anti-inflammatory effect of corticosteroids and may restore the anti-inflammatory effect of glucocorticoids and thus control the underlying disease process in COPD. A eutectic of the present invention that incorporates theophylline and an inhaled corticosteroid in a stoichiometric and pharmacologically acceptable ratio provided a means to have both active ingredients fully co-located in the entire volume of the lung. Furthermore due to the appreciable suppression in melting point (50K for theophylline and 34K for budesonide as shown in Example 5 and FIG. 11) when compared with both active ingredients there is a proportionate increase in rate of dissolution and equilibrium solubility when comparing the eutectic composition to each active ingredient. This can have dramatic effects on the uptake, rate of response and pharmacological effects when administered to patients with asthma and COPD.

The use of Long Acting β2-Agonists (LABAs) has long been a key medication to treat the bronchoconstrictive elements of asthma and COPD. Trials have highlighted that the addition of LABAs to the anticholinergic compound ipratropium bromide is more effective than either agent used alone. The combination of a LABA and anticholinergic (preferably a long-acting muscarinic antagonist (LAMA)) is now an important combination therapy for dealing with asthma and COPD.

The pharmaceutical composition may comprise two pharmacologically active ingredients in a eutectic composition, wherein the pharmacologically active ingredients are a β2-agonist and an anticholinergic, preferably a long acting β2-agonist and a long acting muscarinic antagonist.

In a preferred embodiment of the present invention eutectic compositions can be obtained from any combination of LABA and LAMA whereby a specific combination of the LABA and LAMA has maximum interaction between the two crystalline species yielding homogeneity and a single defined melting point. Examples are given for:

| LABA | LAMA |
| --- | --- |
| Salmeterol xinafoate | Glycopyrronium bromide |
| Formoterol fumarate | Glycopyrronium bromide |
| Indacaterol maleate | Glycopyrronium bromide |
| Salmeterol xinafoate | Tiotropium bromide |
| Formoterol fumarate | Tiotropium bromide |
| SABA | |
| Fenoterol hydrobromide | Glycopyrronium bromide |

Particularly preferred combinations of a β2-agonist and an anticholinergic are albuterol and ipratropium bromide, formoterol fumarate and glycopyrronium bromide, salmeterol xinafoate and glycopyrronium bromide, formoterol fumarate and aclidinium bromide, olodaterol and tiotropium bromide, vilanterol and umeclidinium bromide, vilanterol and glycopyrronium bromide, indacaterol maleate and glycopyrronium bromide, salmeterol xinafoate and tiotropium bromide, formoterol fumarate and tiotropium bromide, and, fenoterol hydrobromide and glycopyrronium bromide.

The preferred molar ratio of β2-agonist to anticholinergic is 10:1 to 1:10, preferably 9:1 to 1:9, preferably 4:1 to 1:4, preferably 2:1 to 1:1, preferably 1:1.

The use of eutectic composition combination particles or combination particles containing part eutectic composition and part excess of one of the components offers an alternative approach for concurrent delivery and co-location of both drugs within the lung rather than making use of a dimer molecule in which both pharmacologies are present (these molecules are known as M3 antagonist-beta2 agonist (MABA) bronchodilators) in the same molecule and so both moieties are covalently bonded to each other.

The pharmaceutical composition may comprise two pharmacologically active ingredients in a eutectic composition, wherein the pharmacologically active ingredients are a corticosteroid and a β2-agonist.

The concurrent delivery of a corticosteroid and a β2-agonist, preferably a LABA is an important medication to treat both the inflammatory and bronchoconstrictive elements of asthma. This superior control is attributed to the mutual synergistic actions of the drugs when taken together, including the activation of the glucocorticoid receptor by the LABA and its effects on other cellular functions related to inflammation in asthma. The addition of a LABA not only reduces exacerbations but improves lung function and symptom control to a greater extent than either component alone. The co-location of actives from a physical mixture is likely to occur randomly when derived from the same cloud emitted from a DPI or pMDI. This approach helps achieve enhanced synergy and additive efficacy on the key target cells and pathologies of inflammation and bronchoconstriction leading to lower doses and improved safety and adherence.

Corticoteroids suitable for forming a eutectic with a LABA include mometasone furoate; beclomethasone dipropionate; budesonide; fluticasone propionate; fluticasone furoate; cliclesonide flunisolide; and triamcinolone acetonide, whereby a specific combination of the steroid and LABA has maximum interaction between the two crystalline species yielding homogeneity and a single defined melting point. Similarly LABAs suitable for forming a eutectic with a corticosteroid include formoterol fumarate, salmeterol xinafoate, and newer entities such as carmoterol, indacaterol, and vilanteril trifenitate.

The pharmaceutical composition may comprise two pharmacologically active ingredients in a eutectic composition, wherein the pharmacologically active ingredients are a corticosteroid and an anticholinergic, preferably a LAMA.

The pharmaceutical composition may comprise two pharmacologically active ingredients in a eutectic composition, wherein the pharmacologically active ingredients are two or more anti-tussive drug substances.

The pharmaceutical composition may comprise two pharmacologically active ingredients in a eutectic composition, wherein the pharmacologically active ingredients are two or more antihistamines.

The pharmaceutical composition may comprise two pharmacologically active ingredients in a eutectic composition, wherein the pharmacologically active ingredients are two or more decongestants.

The pharmaceutical composition may comprise two pharmacologically active ingredients in a eutectic composition, wherein the pharmacologically active ingredients are independently selected from anti-tussive drug substances, antihistamines and antihistamines.

The pharmaceutical composition may comprise two pharmacologically active ingredients in a eutectic composition, wherein the pharmacologically active ingredients are two or more PDE I-VI inhibitors.

The pharmaceutical composition may comprise two pharmacologically active ingredients in a eutectic composition, wherein the pharmacologically active ingredients are two or more PDE IV inhibitors.

The pharmaceutical composition may comprise two pharmacologically active ingredients in a eutectic composition, wherein the pharmacologically active ingredients are two calcium blockers.

According to the invention there is provided a process for preparing compositions of the present invention. The process comprises providing two pharmacologically active ingredients and:

i) dissolving the two pharmacologically active ingredients in a solvent, removing the solvent; and forming particles of the eutectic composition; or ii) forming a melt of the two active pharmaceutical ingredients, solidifying the melt and forming particles of the eutectic composition; or iii) forming a melt of a first active pharmaceutical ingredient and introducing a solution of a second active pharmaceutical ingredient into the melt, solidifying the resulting composition; and forming particles of the eutectic composition; or iv) subjecting the two pharmacologically active ingredients to mechanical comminution to form particles of the eutectic composition;

wherein the pharmacologically active ingredients are each independently selected from $\beta_2$ agonists, anticholinergics, corticosteroids, methylxanthine compounds, antihistamines, decongestants, anti-tussive drug substances, PDE I-VI inhibitors, calcium blockers, tobramycin or ciprofloxacin and salts, esters, polymorphs, hydrates or solvates thereof.

When the process comprises iv) subjecting the two pharmacologically active ingredients to mechanical comminution to form particles of the eutectic composition, the mechanical comminution is preferably by mechanical micronisation, milling, jet milling, grinding, or mixtures thereof. When this process is used, it is necessary to provide sufficient force to form the eutectic mixture. Simply blending two pharmacologically active ingredients will not inevitably result in a eutectic composition.

The process may further comprise treating the particles of the eutectic composition with a non-solvent therefor and applying ultrasound to the particles when they are in contact with the said non-solvent. This further process step has the added advantage of producing highly crystalline particles and is disclosed in WO2010/007447, which is incorporated by reference in its entirety. This is described as the UMAX method; an acronym for Ultrasound Mediated Amorphous to Crystalline transition. Preferably, the composition is dry when the particles of the eutectic composition are treated with a non-solvent. This means that they are preferably substantially free from solvent, including non-solvents, water and organic solvents. This means the particles of the eutectic composition are substantially free of free water or solvent. By substantially free from solvent it is meant that the particles of the eutectic composition contain less than 5% by weight of solvent, more preferably less than 4%, more preferably less than 3%, more preferably less than 2%, more preferably less than 1%, more preferably less than 0.5%, more preferably less than 0.1% by weight of solvent.

As used herein, a non-solvent is one in which the solid material is soluble in an amount of less than 0.1 mg per ml at 25° C., preferably less than 0.05 mg per ml at 25° C., preferably less than 0.01 mg per ml at 25° C.

Conversely, as used herein, a solvent is one in which the solid material is soluble in an amount of greater than 0.1 mg per ml at 25° C., preferably greater than 0.5 mg per ml at 25° C., preferably greater than 1 mg per ml at 25° C., preferably greater than 5 mg per ml at 25° C., preferably greater than 10 mg per ml at 25° C.

The process preferably comprises:
(i) forming a solution of the two pharmacologically active ingredients in a solvent;
(ii) subjecting the solution to a process selected from the group consisting of rapid precipitation, freeze drying, lyophilisation, rapid expansion of supercritical solutions, spray drying or mixtures thereof, wherein the said dissolved pharmacologically active ingredients are converted into a substantially dry solid material;
(iii) optionally isolating the solid material from the liquid and/or gaseous components of the process of step (ii);
(iv) treating said dry solid material from step (ii) or step (iii) with a non-solvent therefor;
(v) applying ultrasound to the solid material from step (iv) when it is in contact with said non-solvent; and
(vi) optionally separating and/or drying the resultant solid material from step (v).

Preferably the process is sequential, and steps (iv) and (v) take place immediately after step (ii).

In such a process, step (ii) preferably comprises spray drying of the solution of the pharmacologically active ingredients. Conventional spray drying may be used. In the spray drying process, the solid material produced is usually substantially amorphous.

Preferably, after the application of step (ii), the material going into step (iii) or (iv) is substantially amorphous, for example, less than 50% crystalline, more preferably less than 40% crystalline, more preferably less than 25% crystalline, more preferably less than 10% crystalline, more preferably less than 5% crystalline, for example less than 1% crystalline.

In step (iv) the term treating means exposing the dry solid material to a non-solvent. This may take place in the same or a separate vessel to the one used to collect the material produced by step (ii). Preferably, the amount of non-solvent is greater than the amount of solid material. For example, the weight ratio of solid material to non-solvent in step (iv) is preferably in the range of 1:100, more preferably 1:10, for example 1:2, 1:3, 1:4, 1:5, etc.

Preferably, the solid material produced by step (ii) and/or step (iii) is substantially dry. This means that preferably all of (100%) of the solid material entering process step (iv) is preferably substantially free from solvent, including water and organic solvents (wherein the term "substantially free from solvent" is defined above).

For any given solid material, the skilled person is capable of determining suitable solvents therefor, without burden. Some examples of solvent suitable for certain solid materials are as follows. Volatile organic solvents such as methanol, ethanol, dichloromethane, ethyl acetate, acetone, 2-propanol and non-organic solvents such as water would be typical solvents for pharmaceutically active ingredients.

An alternative process in WO 2010/007447 for producing particles of the present invention comprises:
(a) subjecting the two pharmacologically active ingredients to mechanical micronization comminution, preferably by milling, jet milling, grinding or mixtures thereof;
(b) treating said pharmacologically active ingredients from step (a) with a non-solvent therefor;
(c) applying ultrasound to the solid composition from step (b) when it is in contact with said non-solvent; and
(d) optionally separating and/or drying the resultant solid composition from step (c).

An alternative process for preparing the pharmaceutical composition of the invention, comprising contacting a solution of both or all solid pharmacologically active ingredients with a solvent in which the solid materials are insoluble or poorly soluble (antisolvent); and applying ultrasound to the mixture of solvent/solution and antisolvent to effect rapid crystallization and dispersion of the microcrystals the composition. Such a method has been described in WO 2008/114052.

The pharmaceutical compositions of the present invention can be administered by a dry powder inhaler, a pressurised metered dose inhaler, or a breath activated nasal inhaler. The invention therefore provides a dry powder inhaler, a pressurized metered-dose inhaler or a breath activated nasal inhaler comprising a composition of the invention.

The pharmaceutical compositions of the present invention may also comprise excipients such as carbohydrates especially monosaccharides such as fructose, glucose and galactose; reducing disaccharides such as lactose, non-reducing disaccharides such as sucrose and trehalose; non-reducing oligosaccharides such as raffinose and melezitose; non reducing starch derived polysaccharides products such as maltodextrins, dextrans and cyclodextrins; and non-reducing alditols such as mannitol and xylitol. Further suitable excipients include cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). Mixtures of two or more of any of the above excipients are also envisaged.

The invention is now described in the following non-limiting Examples.

EXAMPLES

Example 1

Glycopyrronium Bromide (GP)

Formoterol Fumarate Dihydrate (FFD)

Binary mixtures of GB/FFD in ratios (w/w) of 100/0, 90/10, 80/20, 70/30, 60/40, 50/50, 40/60, 30/70, 20/80, 10/90 and 0/100 were prepared for thermal analysis. Each mixture was ground for 15 minutes using mortar and pestle. Samples were analysed by melting point apparatus (MPA100 Optimelt, SRS U.S.A) and Differential Scanning Calorimetery (DSC). The grinding procedure was continued for a further 15 minutes and the DSC analysis repeated to ensure thorough grinding had been accomplished. A graphical representation of temperature of clear melting (solidus and liquidus curve) and molar ratio was used to define the lowest melting point (the eutectic point) and hence the molar ratio of the eutectic composition.

Figure 1:
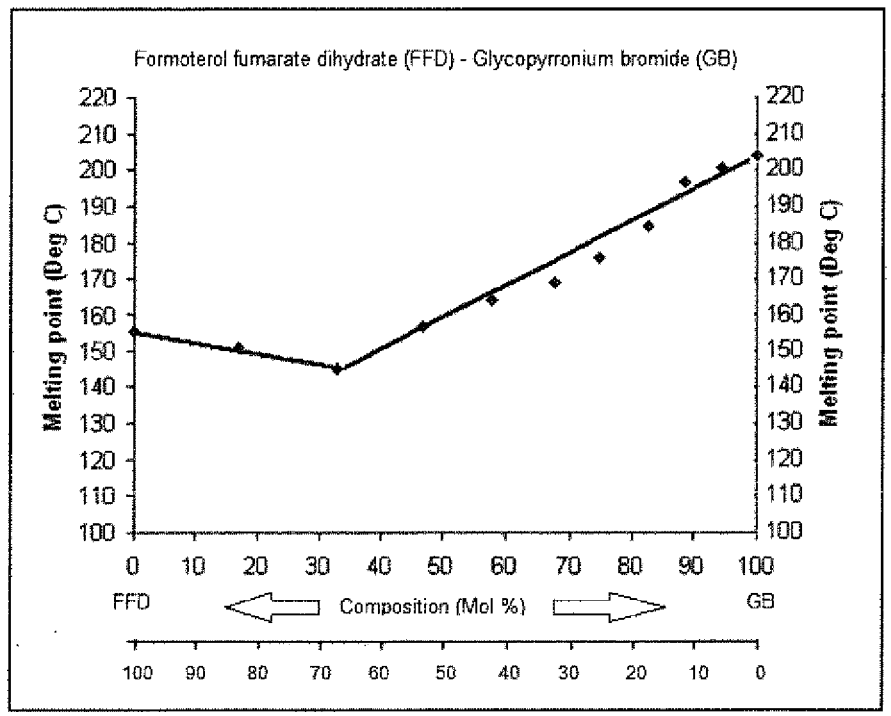
FIG. 1 shows the experimentally determined binary phase diagram for formoterol fumarate dihydrate (FFD) and glycopyrronium bromide (GB) in various molar ratios

Referring to FIG. 1 the binary phase diagram for ground mixtures of formoterol fumarate dihydrate (FFD) and glycopyrronium bromide (GB) shows a characteristic melting transition (solidus-liquidus) to clear liquid at approximately 147° C. for the eutectic composition yielding a single homogenous melting at approximately 2 moles of FFD:1 mole of GB.

Figure 2:
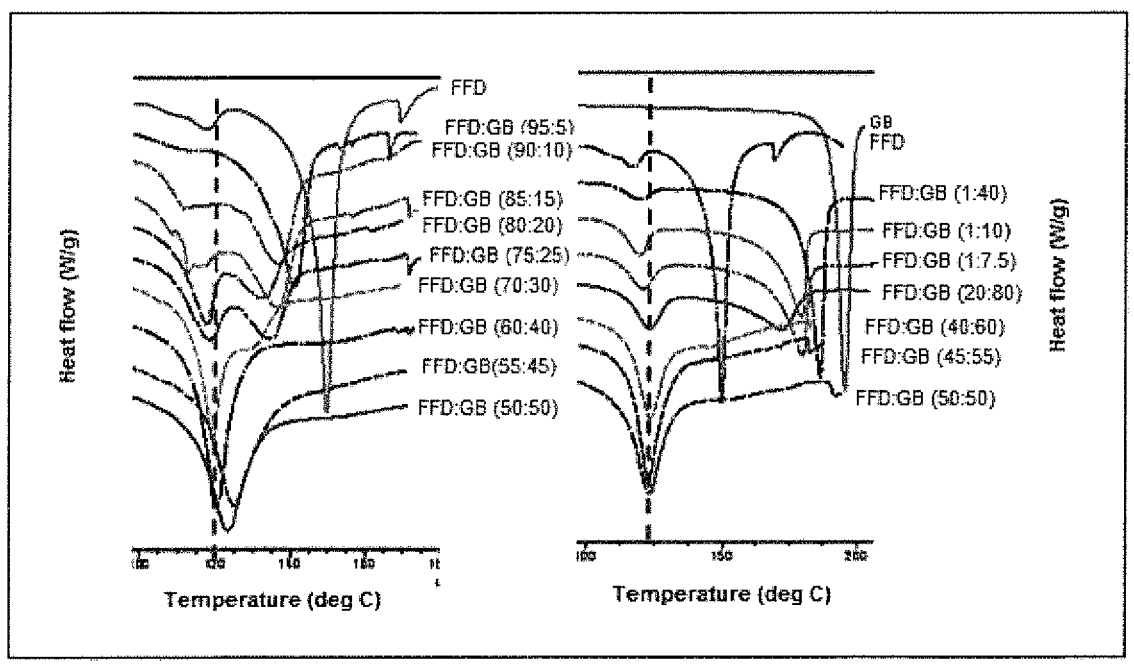
FIG. 2 shows the melting point data and endotherm (negative peak) for ground mixtures of formoterol fumarate dihydrate (FFD) and glycopyrronium bromide (GB) in various mass ratios

Referring to FIG. 2 the melting point and endotherm (negative peak) for ground mixtures of formoterol fumarate dihydrate (FFD) and glycopyrronium bromide (GB) shows a characteristic melting endotherm at with maximum depression at approximately 124° C. onset for the eutectic composition with complete loss of the endotherm associated with FFD (148° C.) and GB (193° C.). Because of the intimate association of the two crystalline structures and effects of Lifshitz-van der Waals forces the melting points of the pure components are also suppressed with respect to the ever increasing proportion of the other component.

UMAX microcrystalline particles of glycopyrronium bromide and formoterol fumarate dihydrate were prepared by a method in accordance with WO 2010/007447. Glycopyrronium bromide and formoterol fumarate dihydrate at the eutectic ratio were dissolved in methanol (300 mL). The resulting solution was spray dried using a Buchi-B290 spray dryer fitted with a twin-fluid nozzle with 0.7 mm orifice with a supporting nitrogen flow rate of 35-40 m$^3$/h (100% Aspirator), at flow rate of 9 mL/min (30% Pump) and nozzle clean setting 2. Inlet temperature was 80° C. and outlet temperature 45° C. Diisopropyl ether (300 mL) was charged to a stirred 500 mL maximum volume ultrasonic vessel connected to the bottom of the B-290 cyclone and thermoregulated at 5° C. The spray dried product was collected into the ultrasonic vessel operating at 40 W continuous power for 2 hr, following the addition of the first particles of amorphous material. The particles of eutectic composition were recovered by filtration.

Figure 3:
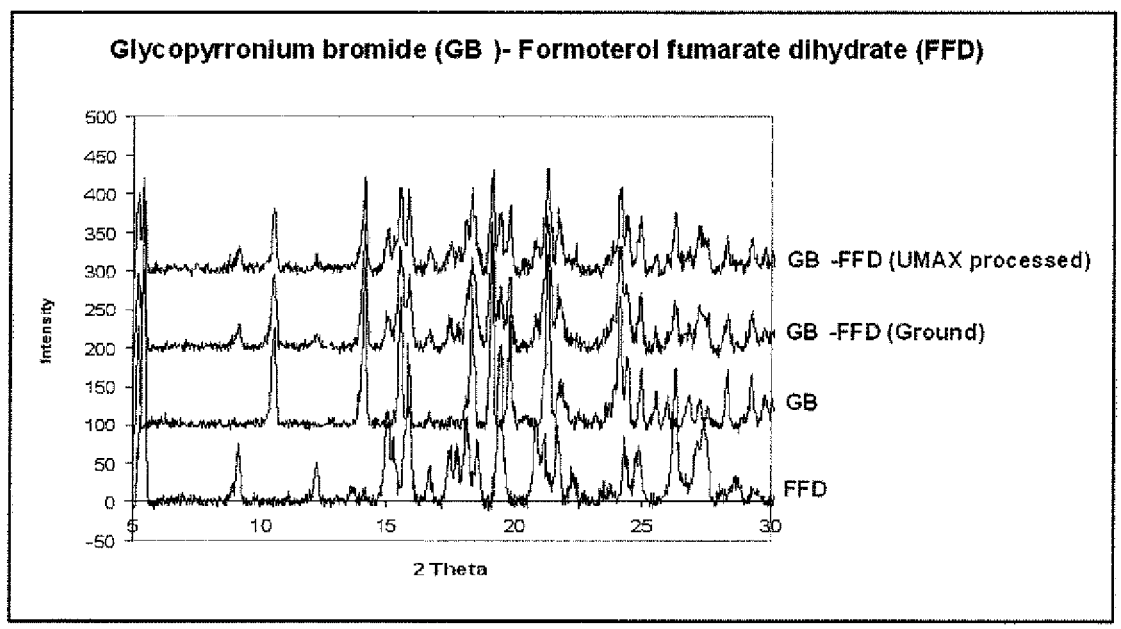
FIG. 3 shows the powder X-ray diffractograms for microcrystalline particles of the eutectic composition, prepared by grinding and UMAX as described in WO2010/007447, of formoterol fumarate dihydrate (FFD) and glycopyrronium bromide (GB)

Referring to FIG. 3 the XRPD patterns of GB/FFD eutectic material prepared by grinding and UMAX processing (as defined in WO 2010/007447) shows that XRPD diffractograms of GB and FFD are similar to those reported previously. The XRPD diffractograms of ground product and that of UMAX processed material are identical to physical mixture of GB and FFD indicating that the crystal lattice of both the components are maintained.

Differential Scanning Calorimetry (DSC)

DSC experiments were performed with a DSC Q2000 V24.2 build 107 (TA Instruments, UK). Approximately 1-3 mg of material was weighed into the sample pan of the DSC and subjected to heating ramp of 25° C./min add heated to up to 200° C. The DSC measurement was carried out using the following steps.
- Instrument DSC Q2000 V24.2 Build 107
- Module DSC Standard Cell RC
- Sample PXLB040-83
- Size 1.2800 mg
- Method heating experiment 25° C.-min
- Weighed sample is heated at rate of 25° C./Min to 200° C.

Determination of Melting Profiles

Melting profile of mixtures were monitored using melting point apparatus (MPA100 Optimelt, SRS U.S.A). The sample was loaded into a melting point capillary tube by pressing the open end of the tube into the powder. The powder was packed into the closed end of the tube by tapping the closed end carefully against the bench top. The cycle was repeated until 1-2 mm of sample in depth could be seen through the tube. The sample was heated at a rate of 20° C. per minute until it melted. The temperature at which liquid first appeared in the bulk of the sample and the temperature at which the entire sample became a liquid were recorded. The apparatus detects melting by light transmittance. The onset is defined as 10% light transmittance, single point is defined as 50% light transmittance and clear liquid is defined as 100% light transmittance.

Example 2

Glycopyrronium Bromide (GB)

Salmeterol Xinafoate (SX)

Binary mixtures of GP/SX in ratios (w/w) of 100/0, 90/10, 80/20, 70/30, 60/40, 50/50, 40/60, 30/70, 20/80, 10/90 and 0/100 were prepared for thermal analysis by following the method of Example 1. The determination of melting profiles using the Optimelt melting point apparatus was carried out in an identical manner to that shown in Example 1.

Figure 4:
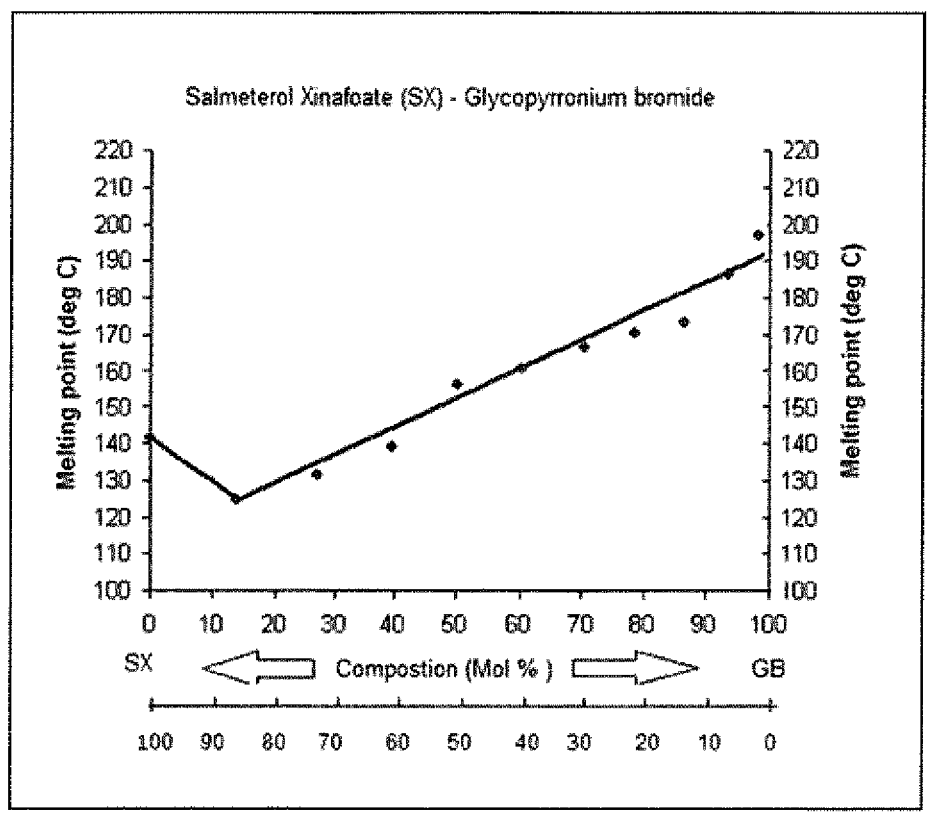
FIG. 4 shows the experimentally determined binary phase diagram for salmeterol xinafoate (SX) and glycopyrronium bromide (GB) in various molar ratios

Referring to FIG. 4 the binary phase diagram for ground mixtures of salmeterol xinafoate (SX) and glycopyrronium bromide (GB) shows a characteristic melting transition (solidus-liquidus) to clear liquid at approximately 124° C. for the eutectic composition yielding a single homogenous melting at approximately 6 moles of SX:1 mole of GB.

Figure 5:
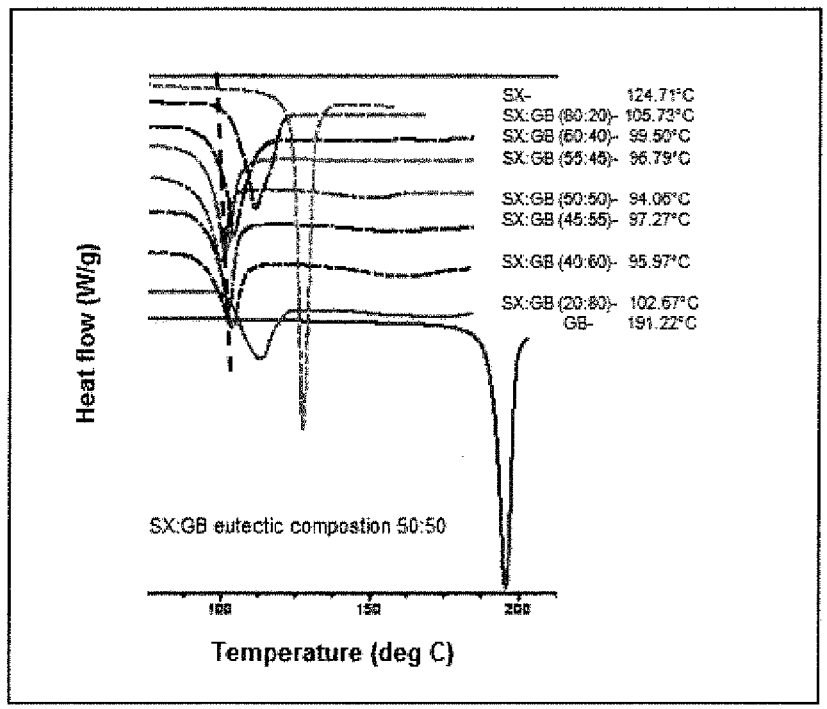
FIG. 5 shows the melting point and endotherm (negative peak) for ground mixtures of salmeterol xinafoate (SX) and glycopyrronium bromide (GB) in various mass ratios

Referring to FIG. 5 the melting point and endotherm (negative peak) for ground mixtures of salmeterol xinafoate (SX) and glycopyrronium bromide (GB) shows a characteristic melting endotherm with maximum depression at approximately 100° C. onset for the eutectic composition with complete loss of the endotherm associated with SX (124° C.) and GB (191° C.). The melting points of the pure components SX and FF is also suppressed with respect to the ever increasing proportion of the other component.

UMAX Microcrystalline particles of glycopyrronium bromide and salmeterol xinafoate were prepared by a method in accordance with WO 2010/007447. Glycopyrronium bromide and salmeterol xinafoate at the eutectic composition were dissolved in methanol (300 mL). The resulting solution was spray dried using a Buchi-B290 spray dryer fitted with a twin-fluid nozzle with 0.7 mm orifice with a supporting nitrogen flow rate of 35-40 m$^3$/h (100% Aspirator), at flow rate of 9 mL/min (30% Pump) and nozzle clean setting 2. Inlet temperature was 80° C. and outlet temperature 45° C. Cyclohexane (300 mL) was charged to a stirred 500 mL maximum volume ultrasonic vessel connected to the bottom of the B-290 cyclone and thermoregulated at 5° C. The spray dried product was collected into the ultrasonic vessel operating at 40 W continuous power for 2 hr, following the addition of the first particles of amorphous material. The particles of eutectic composition were recovered by filtration.

Figure 6:
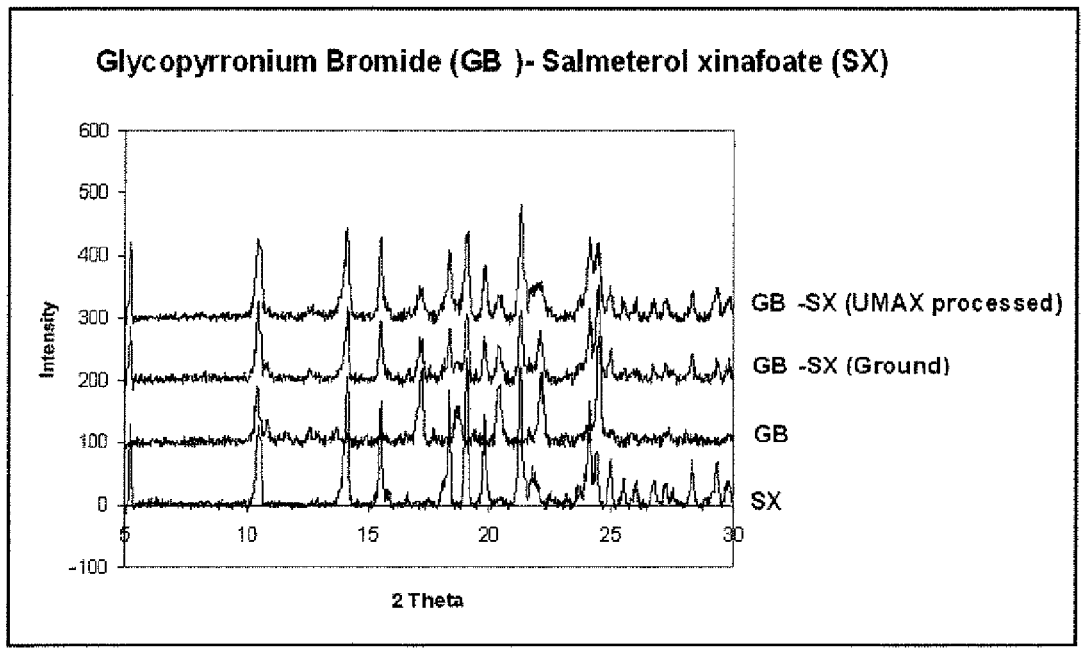
FIG. 6 shows the powder X-ray diffractograms for microcrystalline particles of the eutectic composition, prepared by grinding and UMAX as described in WO2010/007447, of salmeterol xinafoate (SX) and glycopyrronium bromide (GB)

Referring to FIG. 6 the XRPD patterns of GB, SX and the GB:SX eutectic materials prepared by grinding and UMAX processing shows that the XRPD diffractograms of GB and SX are similar to those reported previously. The XRPD diffractograms of ground product at the eutectic composition and that of UMAX processed material at the eutectic composition are identical to physical mixture of GB and SX indicating that the crystal lattice of both the components are maintained.

Example 3

Glycopyrronium Bromide (GP)

Fenoterol Hydrobromide (FHBr)

Binary mixtures of GB/FHBr in ratios (w/w) of 100/0, 90/10, 80/20, 70/30, 60/40, 50/50, 40/60, 30/70, 20/80, 10/90 and 0/100 were prepared for thermal analysis by following the method of example 1. The determination of melting profiles using the Optimelt melting point apparatus was carried out in an identical manner to that shown in Example 1. The measured temperatures are shown.

| GB mass % | FHBr mass % | Onset T ° C. | Clear point T ° C. |
|---|---|---|---|
| 0 | 100 | 234.7 | 246.1 |
| 10 | 90 | 196.5 | 241.4 |
| 20 | 80 | 150.1 | 240.5 |
| 30 | 70 | 142.6 | 232.9 |
| 40 | 60 | 139.5 | 240.1 |
| 50 | 50 | 141 | 239.9 |
| 60 | 40 | 140.5 | 191.5 |
| 70 | 30 | 144.8 | 161.3 |
| 80 | 20 | 149.2 | 177.1 |
| 90 | 10 | 175.1 | 190.2 |
| 100 | 0 | 195.4 | 236.9 |

Figure 7:
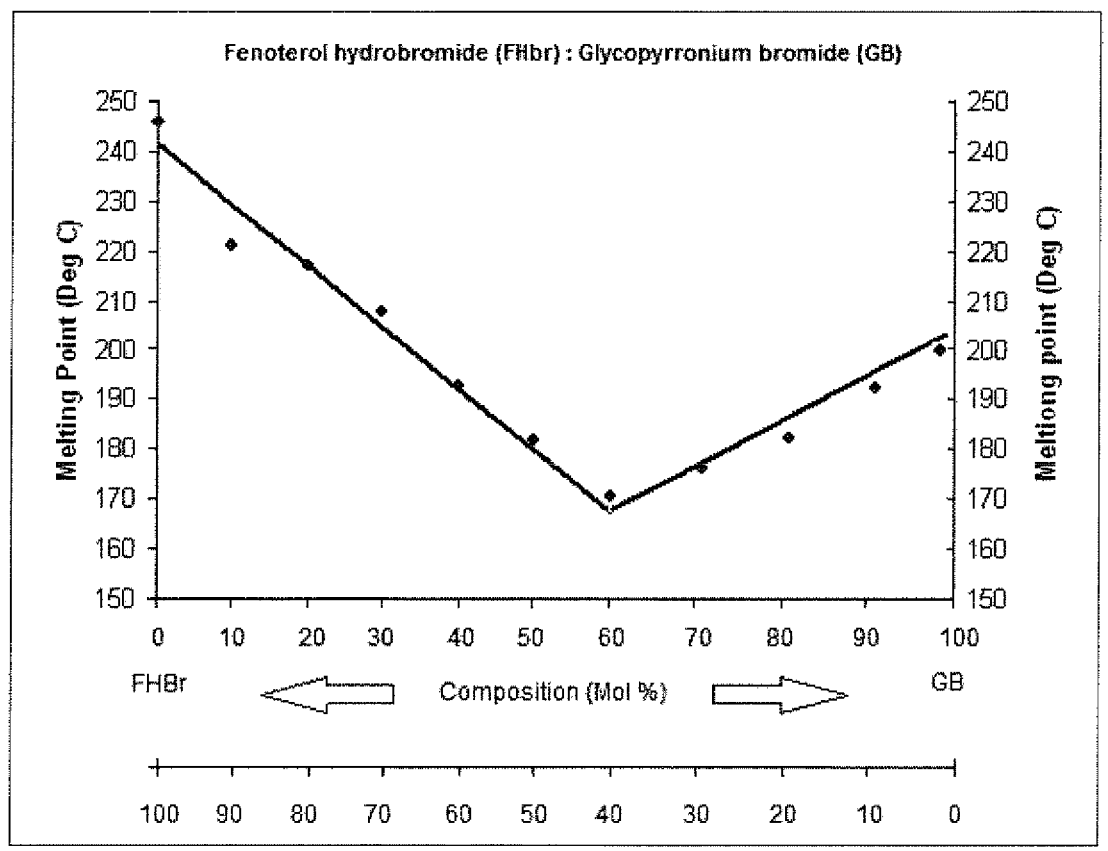
FIG. 7 shows the experimentally determined binary phase diagram for fenoterol hydrobromide (FHBr) and glycopyrronium bromide (GB) in various molar ratios

Referring to FIG. 7 the binary phase diagram for ground mixtures of fenoterol hydrobromide (FHBr) and glycopyrronium bromide (GB) shows a characteristic melting transition (solidus-liquidus) to clear liquid at approximately 140° C. for the eutectic composition yielding a single homogenous minimum melting at approximately 2 mole of FHBr:3 moles of GB ratio.

Figure 8:
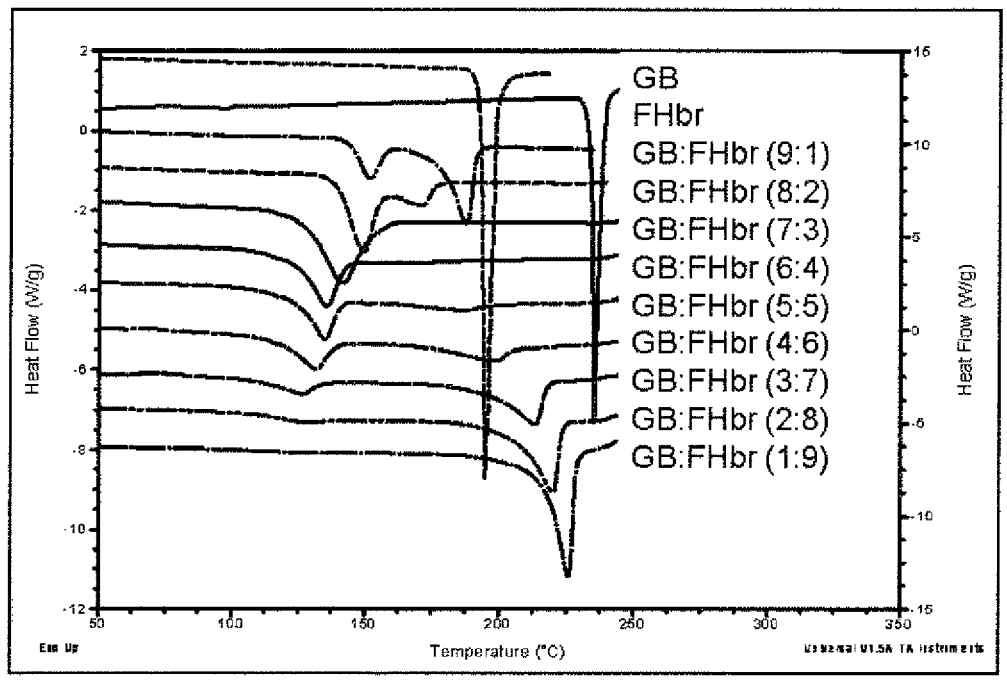
FIG. 8 shows the melting point and endotherm (negative peak) for ground mixtures of fenoterol hydrobromide (FHBr) and glycopyrronium bromide (GB) in various mass ratios

Referring to FIG. 8 the melting point and endotherm (negative peak) ground mixtures of fenoterol hydrobromide (FHBr) and glycopyrronium bromide (GB) shows a characteristic melting endotherm with maximum depression at or around 125° C. onset and 130° C. negative peak for the eutectic composition with complete loss of the endotherm associated with FHBr (235° C.) and GB (195° C.). The melting points of the pure components FHBr and GB is also suppressed with respect to the ever increasing proportion of the other component.

Example 4

Glycopyrronium Bromide (GB)

Indacaterol Maleate (IM)

Binary mixtures of GB/IM in ratios (w/w) of 100/0, 90/10, 80/20, 70/30, 60/40, 50/50, 40/60, 30/70, 20/80, 10/90 and 0/100 were prepared for thermal analysis by following the method of Example 1.

The determination of melting profiles using the Optimelt melting point apparatus was carried out in an identical manner to that shown in Example 1. The measured temperatures are shown.

| GB mass % | IM mass % | Onset T ° C. | Clear point T ° C. |
|---|---|---|---|
| 0 | 100 | 209.5 | 213.6 |
| 10 | 90 | 182.4 | 202.4 |
| 20 | 80 | 181.2 | 203.4 |
| 30 | 70 | 175.9 | 204.6 |
| 40 | 60 | 174.3 | 203.2 |
| 50 | 50 | 170.7 | 203.4 |
| 60 | 40 | 165.1 | 203.5 |
| 70 | 30 | 166.7 | 200.2 |
| 80 | 20 | 172.7 | 189.4 |
| 90 | 10 | 175.5 | 187.4 |
| 100 | 0 | 195.1 | 199.7 |

Figure 9:
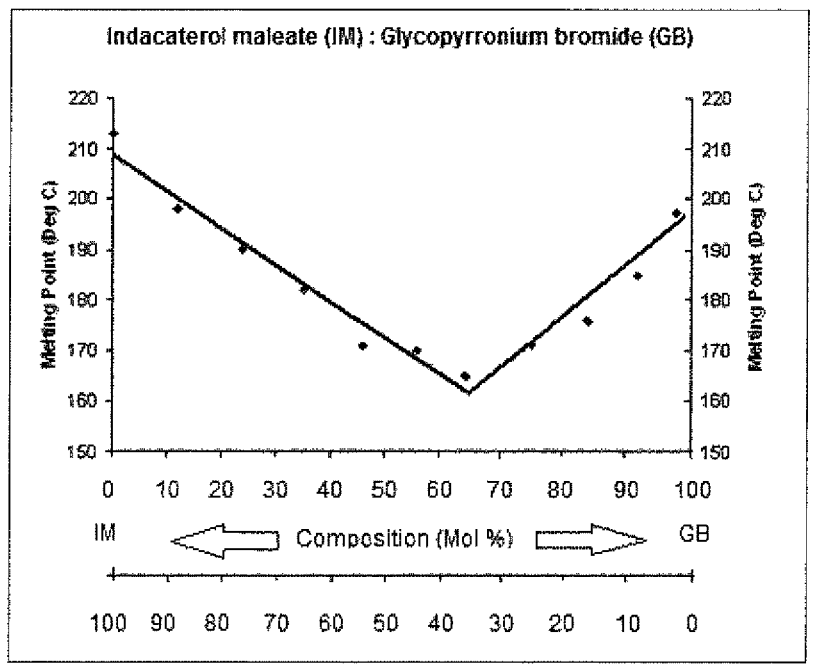
FIG. 9 shows the experimentally determined binary phase diagram for indacaterol maleate (IM) and glycopyrronium bromide (GB) in various molar ratios

Referring to FIG. 9 the binary phase diagram for ground mixtures of indacaterol maleate (IM) and glycopyrronium bromide (GB) shows a characteristic melting transition (solidus-liquidus) to clear liquid at approximately 163° C. for the eutectic composition yielding a single homogenous minimum melting at approximately 1:2 mole ratio for IM:GB.

Figure 10:
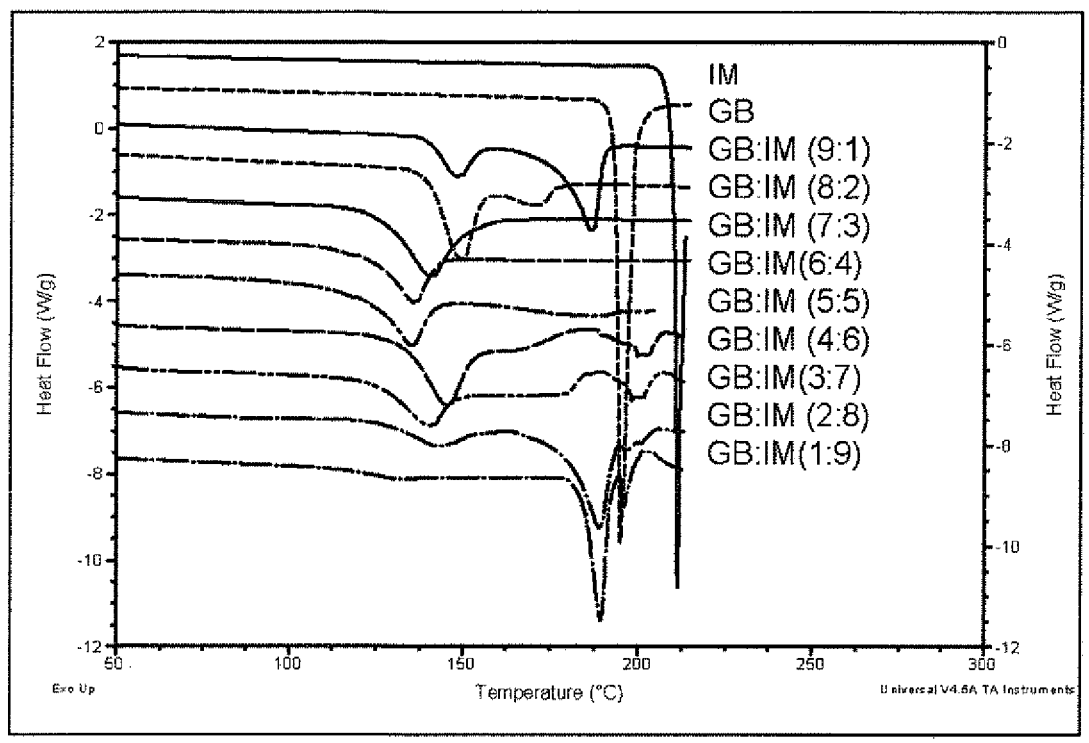
FIG. 10 shows the melting point and endotherm (negative peak) for ground mixtures of indacaterol maleate (IM) and glycopyrronium bromide (GB) in various mass ratios

Referring to FIG. 10 the melting point and endotherm (negative peak) ground mixtures of indacaterol maleate (IM) and glycopyrronium bromide (GB) shows a characteristic melting endotherm with maximum depression at or around 125° C. onset and 135° C. negative peak for the eutectic composition with complete loss of the endotherm associated with 1M (210° C.) and GB (195° C.). The melting points of the pure components IM and GB is also suppressed with respect to the ever increasing proportion of the other component.

UMAX Microcrystalline particles of glycopyrronium bromide and indacaterol maleate were prepared by a method in accordance with WO 2010/007447. Glycopyrronium bromide and indacaterol maleate at the eutectic composition were dissolved in methanol (300 mL) at 70° C. The resulting solution was spray dried using a Buchi-B290 spray dryer fitted with a twin-fluid nozzle with 0.7 mm orifice with a supporting nitrogen flow rate of 35-40 m$^3$/h (100% Aspirator), at flow rate of 9 mL/min (30% Pump) and nozzle clean setting 2. Inlet temperature was 80° C. and outlet temperature 45° C. Diisopropyl ether (300 mL) was charged to a stirred 500 mL maximum volume ultrasonic vessel connected to the bottom of the B-290 cyclone and thermoregulated at 5° C. The spray dried product was collected into the ultrasonic vessel operating at 40 W continuous power for 2 hr, following the addition of the first particles of amorphous material. The particles of eutectic composition were recovered by filtration.

Example 5

Theophylline (TP)

Budesonide (BDS)

Binary mixtures of TP/BDS in ratios (w/w) of 100/0, 90/10, 80/20, 70/30, 60/40, 50/50, 40/60, 30/70, 20/80, 10/90 and 0/100 were prepared for thermal analysis by following the method of Example 1. The determination of melting profiles using the Optimelt melting point apparatus and DSC was carried out in an identical manner to that shown in Example 1. The data is shown.

| | DSC | | Optimelt | | |
|---|---|---|---|---|---|
| Sample | Onset of melting (° C.) | Negative Peak (° C.) | Onset of melting (° C.) | Single (° C.) | Clear liquid (° C.) |
| TP | 271.90 | 273.39 | 273.6 | 277.7 | 281.2 |
| TP:BDS (9:1) | 222.27 | 226.23 | 247.2 | 261.1 | 272.0 |
| TP:BDS (8:2) | 217.12 | 221.67 | 233.1 | 247.6 | 265.8 |
| TP:BDS (7:3) | 216.82 | 221.09 | 225.2 | 240.2 | 261.6 |
| TP:BDS (6:4) | 219.00 | 222.71 | 222.8 | 227.0 | 256.8 |
| TP:BDS (5:5) | 219.41 | 222.52 | 223.3 | 235.9 | 253.6 |
| TP:BDS (4:6) | 217.79 | 222.21 | 221.9 | 224.1 | 243.3 |
| TP:BDS (3:7) | 217.35 | 222.99 | 220.5 | 225.8 | 235.2 |
| TP:BDS (2:8) | 216.80 | 221.89 | 220.4 | 222.8 | 236.3 |
| TP:BDS (1:9) | 218.03 | 220.59 | 221.0 | 224.3 | 242.5 |
| BDS | 249.14 | 256.29 | 253.5 | 258.2 | 265.7 |

UMAX Microcrystalline particles of budesonide and theophylline were prepared by a method in accordance with WO 2010/007447. Theophylline (5 g) was dissolved in glacial (100%) acetic acid (100 mL). Budesonide (5 g) was dissolved in acetone (100 mL). The two solutions were mixed together and the combined solution spray dried spray-dry using a Buchi-B290 spray dryer fitted with a twin-fluid nozzle with 0.7 mm orifice with a supporting nitrogen flow rate of 35-40 m$^3$/h (100% Aspirator), at flow rate of 9 mL/min (30% Pump) and nozzle clean setting 2. Inlet temperature was 110° C. and outlet temperature 38° C. Heptane (300 mL) was charged to a stirred 500 mL maximum volume ultrasonic vessel connected to the bottom of the B-290 cyclone and thermoregulated at 5° C. The spray dried product was collected into the ultrasonic vessel operating at 40 W continuous power for 2 hr, following the addition of the first particles of amorphous material. The particles of eutectic composition were recovered by spray drying the suspension with a Buchi-B8290 as above with inlet temperature is 1100° C. and outlet temperature 50° C.

Figure 11:
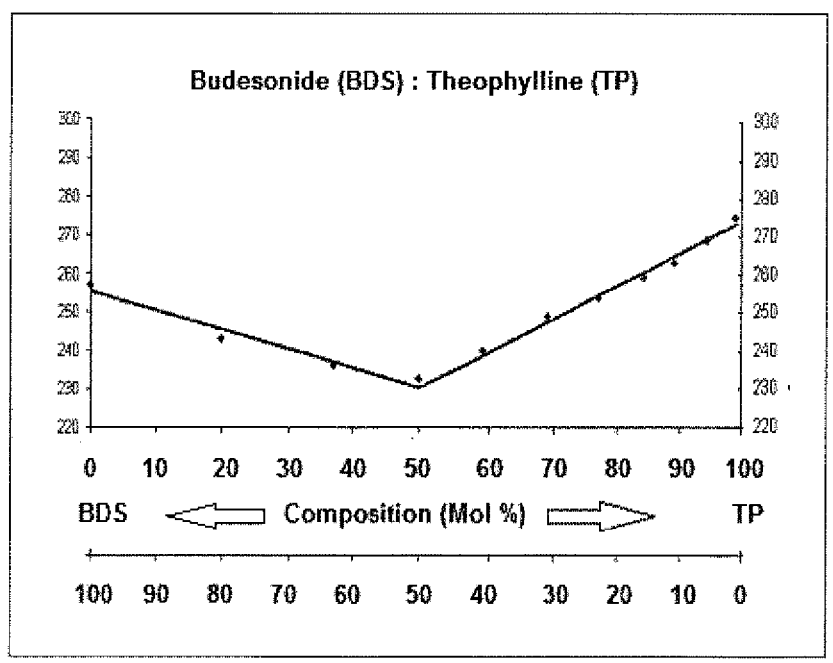
FIG. 11 shows the experimentally determined binary phase diagram for theophylline and budesonide in various molar ratios

Referring to FIG. 11 the binary phase diagram for ground mixtures of theophylline (TP) and budesonide (BDS) shows a characteristic melting transition (solidus-liquidus) to clear liquid at approximately 230° C. for the eutectic composition yielding a single homogenous minimum melting with maximum depression at approximately 1:1 mole ratio for TP:BDS.

Figure 12:
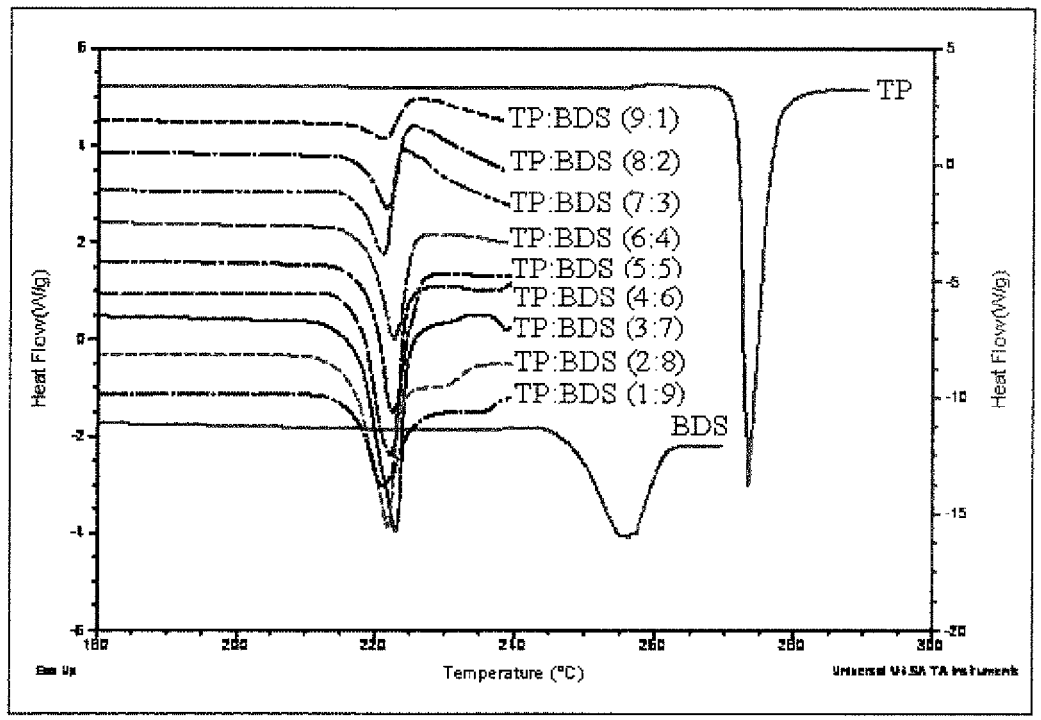
FIG. 12 shows the melting point and endotherm (negative peak) for ground mixtures of theophylline (TP) and budesonide (BDS)

Referring to FIG. 12 the melting point and endotherm (negative peak) for ground mixtures of theophylline (TP) and budesonide (BDS) show a characteristic melting endotherm at approximately 220° C. (onset/peak temperature) for the eutectic composition thus indicating a single homogenous melting at approximately 7:3 mass ratio BDS:TP. This equates to approximately BDS:TP molar ratio of 1:1 whereby BDS molecular weight is 430.5 and TP is 180.2. DSC analysis was ceased at 240° C. due to either complete melting or gross decomposition.

Figure 13:
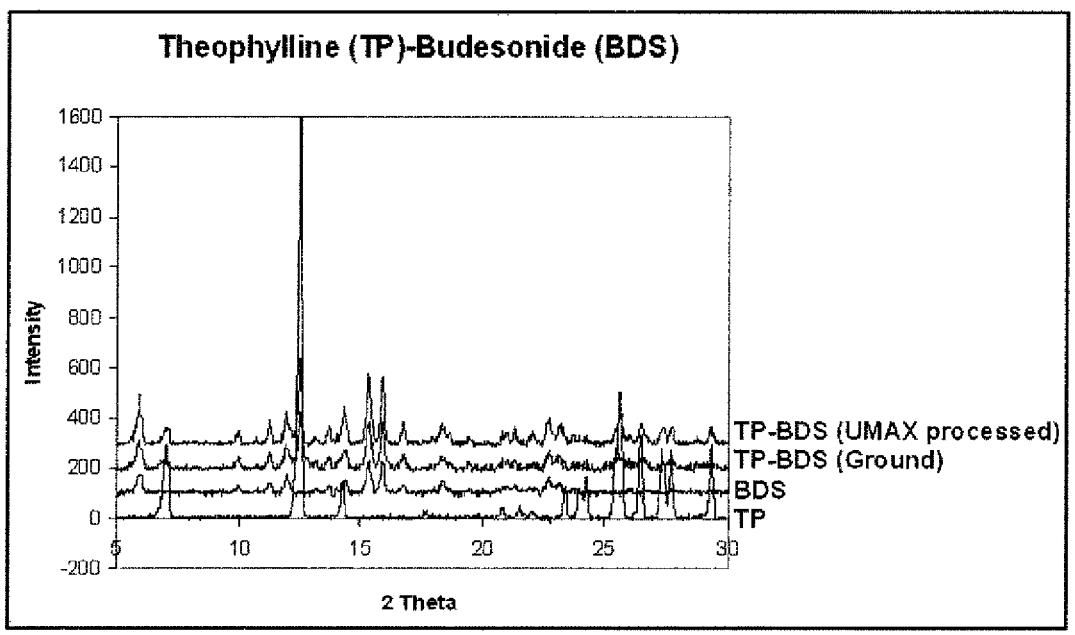
FIG. 13 shows the powder X-ray diffractograms for microcrystalline particles of the eutectic composition, prepared by grinding and UMAX as described in WO02010/007447, of theophylline (TP) and budesonide (BDS)

Referring to FIG. 13 the XRPD patterns of TP, BDS and the (BDS:TP, 7:3 mass ratio) material prepared by grinding and UMAX processing show that the XRPD diffractograms of TP and BDS are similar to those reported previously. The XRPD diffractograms of ground product and that of UMAX processed material are identical to physical mixture of TP and BDS indicating that the crystal lattice of both the components are maintained.

Example 6

Tiotropium Bromide and Formoterol Fumarate Dihydrate

Binary mixture of Tio/FFD in a 1:1 molar ratio was prepared for thermal analysis by following the method of Example 1. The determination of melting profiles using the Optimelt melting point apparatus and DSC was carried out in an identical manner to that shown in Example 1. The data is shown below.

|         | Tio     | FD  | Tio-FFD (1:1) molar |
|---------|---------|-----|---------------------|
| MP (° C.) | 228-230 | 45  | ~102                |

Figure 14:
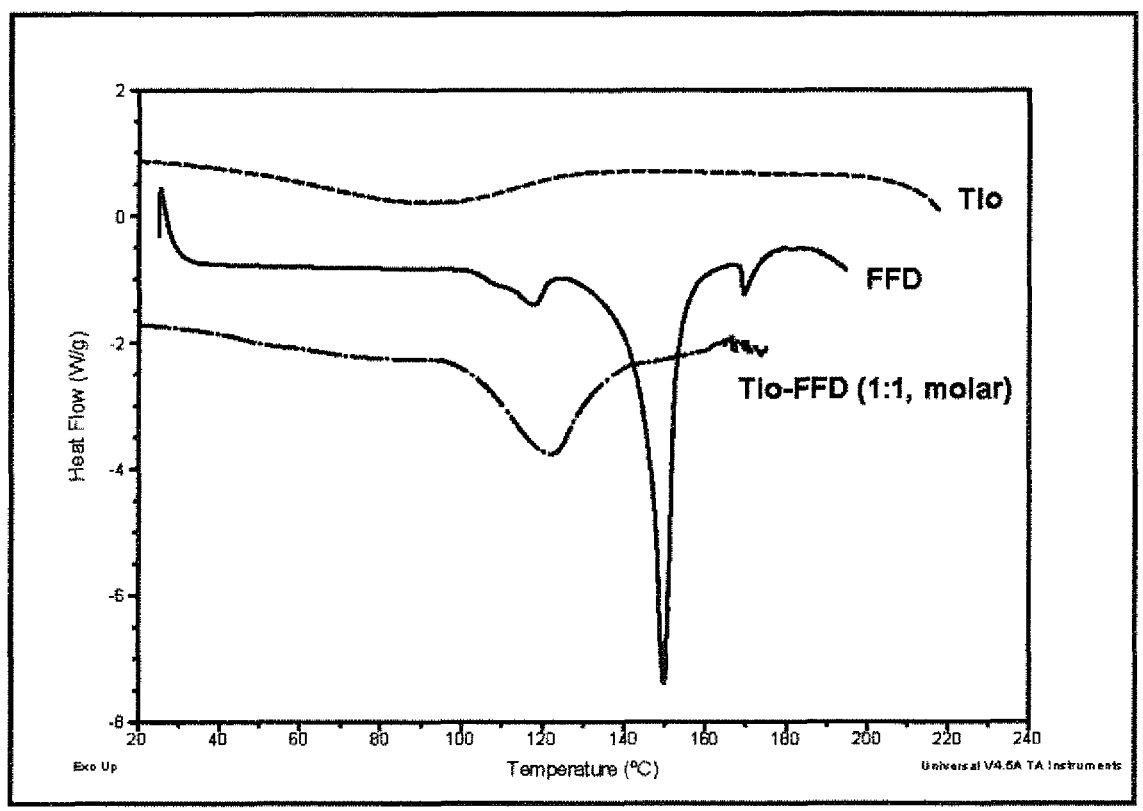
FIG. 14 shows the melting point and endotherm (negative peak) for a 1:1 molar ground mixture of tiotropium bromide (Tio) and formoterol fumarate dihydrate (FFD)

Referring to FIG. 14 the melting point and endotherm (negative peak) for a ground mixture of tiotropium bromide (Tio) and formoterol fumarate dehydrate (FFD) shows a characteristic melting endotherm at approximately 102° C. (onset/peak temperature) for the eutectic composition thus indicating a single homogenous melting for the eutectic composition. Therefore a eutectic is formed at a 1:1 molar ratio.

Example 7

Tiotropium Bromide and Salmeterol Xinofoate

Binary mixture of Tio/SX in a 1:1 molar ratio was prepared for thermal analysis by following the method of Example 1. The determination of melting profiles using the Optimelt melting point apparatus and DSC was carried out in an identical manner to that shown in Example 1. The data is shown below.

|         | Tio     | SX  | Tio-SX (1:1) molar |
|---------|---------|-----|--------------------|
| MP (° C.) | 228-230 | 125 | 104                |

Figure 15:
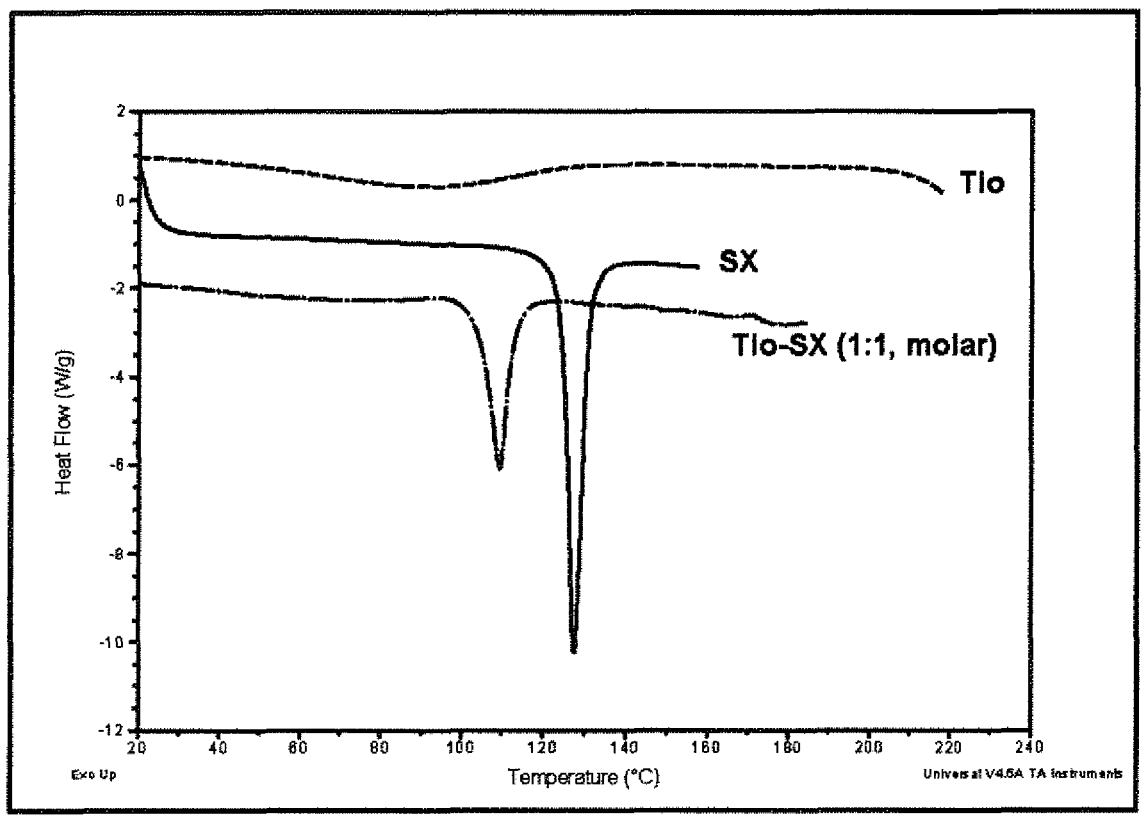
FIG. 15 shows the melting point and endotherm (negative peak) for a 1:1 molar ground mixture of tiotropium bromide (Tio) and salmeterol xinafoate (SX)

Referring to FIG. 15 the melting point and endotherm (negative peak) for a ground mixture of tiotropium bromide (Tio) and salmeterol xinofoate (SX) shows a characteristic melting endotherm at approximately 104° C. (onset/peak temperature) for the eutectic composition thus indicating a single homogenous melting for the eutectic composition. Therefore a eutectic is formed at a 1:1 molar ratio.

The invention claimed is:

1. A pharmaceutical composition comprising a eutectic composition of two pharmacologically active ingredients;
    wherein the pharmacologically active ingredients are a long acting $\beta_2$ agonist and a long acting muscarinic antagonist;
    wherein the composition is formulated for delivery to the lung by inhalation;
    wherein the molor ratio of the two pharmacologically active ingredients is 10:11 to 1:1;
    wherein the melting point of the autectic composition is lower than the melting point of either the long acting $\beta_2$ agonist of the long acting muscarinic antagonist forming the autectic composition.

2. A pharmaceutical composition for use in the treatment of a respiratory disease, the pharmaceutical composition comprising a eutectic composition of two pharmacologically active ingredients;
    wherein the pharmacologically active ingredients are a long acting $\beta_2$ agonist and a long acting muscarinic antagonist;
    wherein the molor ratio of the two pharmacologically active ingredients is 10:1 to 1:1;
    wherein the melting point of the eutectic composition is lower than the melting point of either the long acting $\beta_2$ agonist or the long acting muscarinic antagonist forming the eutectic composition;
    wherein the respiratory disease is a chronic respiratory disease selected from the group consisting of COPD, asthma and cystic fibrosis.

3. A pharmaceutical composition comprising two pharmacologically active ingredients in a eutectic composition;
    wherein the pharmacologically active ingredients are a long acting $\beta_2$ agonist and a long acting muscarinic antagonist;
    wherein the molar ratio of the two pharmacologically active ingredients is 10:1 to 1:1;
    wherein the melting point of the eutectic composition is lower than the melting point of either the on acting $\beta_2$ agonist or the long acting muscarinic antagonist forming the eutectic composition.

4. A composition according to claim 1, further comprising an excess of at least one of the pharmacologically active ingredients, wherein the excess forms less than 50% by weight of the total weight of the said pharmacologically active ingredients present in the composition.

5. A composition according to claim 1, wherein 90% by weight of at least one of the pharmacologically active ingredients is in the eutectic composition.

6. A composition according to claim 1 wherein the eutectic composition is in particulate form.

7. A dry powder inhaler containing a composition according to claim 1.

8. A composition according to claim 6 wherein the mass median aerodynamic diameter is up to 10 μm.

9. A composition according to claim 2, further comprising an excess of at least one of the pharmacologically active ingredients, wherein the excess forms less than 50% by weight of the total weight of the said pharmacologically active ingredients present in the composition.

10. A composition according to claim 2, wherein 90% by weight of at least one of the pharmacologically active ingredients is in the eutectic composition.

11. A composition according to claim 2 wherein the eutectic composition is in particulate form.

12. A composition according to claim 11 wherein the mass median aerodynamic diameter is up to 10 μm.

13. A composition according to claim 3, further comprising an excess of at least one of the pharmacologically active ingredients, wherein the excess forms less than 50% by weight of the total weight of the said pharmacologically active ingredients present in the composition.

14. A composition according to claim 3, wherein 90% by weight of at least one of the pharmacologically active ingredients is in the eutectic composition.

15. A composition according to claim 3 wherein the eutectic composition is in particulate form.

16. A composition according to claim 15 wherein the mass median aerodynamic diameter is up to 10 μm.

17. A composition according to claim 3, wherein the rate of dissolution of the eutectic composition is increased compared to blend of a long acting $\beta_2$ agonist and a long acting muscarinic antagonist.

* * * * *